United States Patent
Krishnan et al.

(10) Patent No.: US 11,651,861 B2
(45) Date of Patent: May 16, 2023

(54) DETERMINING ENGAGEMENT LEVEL OF AN INDIVIDUAL DURING COMMUNICATION

(71) Applicant: International Business Machines Corporation, Armonk, NY (US)

(72) Inventors: Jayanth Krishnan, Cambridge, MA (US); Azka Javaid, Brooklyn, NY (US); Paul R. Bastide, Ashland, MA (US); Fang Lu, Billerica, MA (US)

(73) Assignee: International Business Machines Corporation, Armonk, NY (US)

( * ) Notice: Subject to any disclaimer, the term of this patent is extended or adjusted under 35 U.S.C. 154(b) by 611 days.

(21) Appl. No.: 16/721,066

(22) Filed: Dec. 19, 2019

(65) Prior Publication Data

US 2021/0193316 A1 Jun. 24, 2021

(51) Int. Cl.
| | |
|---|---|
| *G16H 50/20* | (2018.01) |
| *G16H 50/30* | (2018.01) |
| *G10L 15/22* | (2006.01) |
| *G10L 15/18* | (2013.01) |
| *G16H 10/60* | (2018.01) |

(52) U.S. Cl.
CPC ......... *G16H 50/20* (2018.01); *G10L 15/1815* (2013.01); *G10L 15/22* (2013.01); *G16H 10/60* (2018.01); *G10L 2015/225* (2013.01)

(58) Field of Classification Search
CPC ........ G16H 50/20; G16H 10/60; G16H 50/30; G16H 80/00; G10L 15/1815; G10L 15/22; G10L 2015/225
See application file for complete search history.

(56) References Cited

U.S. PATENT DOCUMENTS

| | | |
|---|---|---|
| 6,039,688 A | 3/2000 | Douglas |
| 6,305,377 B1 | 10/2001 | Portwood |
| 6,850,889 B1 | 2/2005 | Zayas, Jr. |

(Continued)

OTHER PUBLICATIONS

"An Evaluation Protocol", Office of Minority Health, U.S. Department of Health and Human Services, Apr. 2008, 108 pps., <https://minorityhealth.hhs.gov/Assets/pdf/Checked/1/Evaluation_Protocol.pdf>.

(Continued)

*Primary Examiner* — Maroun P Kanaan
(74) *Attorney, Agent, or Firm* — Aaron Pontikos (57) ABSTRACT

A plurality of instances of a patient's health condition are received as patient health information from a plurality of sources. Ground-truth health conditions of the patient are generated based on the patient health information and expert review of the patient's level of engagement for each instance of provider assessment. A regression model predicting a probability of patient engagement level with a provider is generated, based on the instances of patient condition assessment and the engagement level expert review associated with each instance. A current set of patient information and natural language processing results of a dialog between the patient and a provider performing a condition assessment of the patient, are received. The current patient information and the dialog are applied to the regression model, determining a probability of patient engagement level. An indicator of the patient engagement level is sent to the provider's computing device.

20 Claims, 4 Drawing Sheets

(56) References Cited

U.S. PATENT DOCUMENTS

| | | | |
|---|---|---|---|
| 7,379,885 | B1 | 5/2008 | Zakim |
| 8,635,086 | B2 | 1/2014 | Blom |
| 2004/0073464 | A1 | 4/2004 | Huang |
| 2005/0055246 | A1 | 3/2005 | Simon |
| 2006/0036471 | A1 | 2/2006 | Sanjay-Gopal |
| 2009/0150181 | A1 | 6/2009 | Gejdos |
| 2015/0193582 | A1 | 7/2015 | Dean |
| 2015/0213224 | A1 | 7/2015 | Amarasingham |
| 2016/0378919 | A1 | 12/2016 | Mcnutt |
| 2018/0018966 | A1* | 1/2018 | Leonard ................. G06N 5/022 |
| 2019/0051376 | A1* | 2/2019 | Gallopyn ............ G06F 21/6245 |
| 2019/0385711 | A1* | 12/2019 | Shriberg ................ G16H 50/20 |

OTHER PUBLICATIONS

"Heart Rate", 9 pps., © FitBit Inc., printed from the Internet on Oct. 7, 2019, <https://dev.fitbit.com/build/reference/web-api/heart-rate/>.

"Vital signs", MedlinePlus Medical Encyclopedia, U.S. National Library of Medicine 8600 Rockville Pike, Bethesda, MD 20894, U.S. Department of Health and Human Services National Institutes of Health, Page last updated: Oct. 2, 2019, 2 pps., <https://medlineplus.gov/ency/article/002341.htm>.

\* cited by examiner

DETERMINING ENGAGEMENT LEVEL OF AN INDIVIDUAL DURING COMMUNICATION

FIELD OF THE INVENTION

The present invention relates generally to the field of communication analysis, and more particularly to determining a level of engagement by individuals responding to questions.

BACKGROUND OF THE INVENTION

Current healthcare service includes a large collection of tools and tests to facilitate determination of medical condition diagnosis, insuring proper treatment. In addition, healthcare providers often rely on first-person accounts and information to determine and evaluate symptoms and medical conditions of patients. Information provided by patients can provide details, identify interactions, and expose associations not always discernable by tests and measurements. When the patient is distracted, the first-person account of a patient impacts the quality-of-care in the determination, evaluation and the treatment of the patient's condition.

The state-of-art evaluation protocols are designed to reduce miss diagnoses of health conditions, however, the quantity of patients requiring healthcare provider attention limits the time available for direct interaction with patients, and healthcare decisions are often made quickly and based on brief assessments. Additionally, combining electronically accessible health information with vital sign measurements offers opportunity to expand and enhance methods used in patient/provider communications.

SUMMARY

Embodiments of the present invention disclose a method, computer program product, and system. The embodiments include a method for determining a level of engagement of a patient with a provider. The method provides for one or more processors to receive information regarding health of a patient from a plurality of sources and including a plurality of instances of the patient's health condition. The one or more processors generate ground-truth health conditions of the patient based on an assessment performed on the plurality of instances of the patient's condition, respectively, in which the assessment includes patient health information and expert review of the level of engagement of the patient for each instance of assessment by a provider. The one or more processors generate a regression model of the patient engagement level, wherein the regression model predicts a probability of engagement by the patient based on the plurality of instances of patient condition assessment and the expert review of the level of engagement associated with each instance of assessment. The one or more processors receive a current set of patient information and results of natural language processing of a dialog between the patient and a provider performing an assessment of the condition of the patient, and environmental conditions monitored during the assessment of the patient by the provider. The one or more processors apply the current set of patient information and the monitoring of the dialog and environmental conditions to the regression model, and the one or more processors, in response to determining a probability of the level of engagement of the patient to the provider, send to the provider, an indicator of the probability of the level of engagement of the patient.

DETAILED DESCRIPTION

Embodiments of the present invention recognize that healthcare providers rely on first-hand account information from patients along with patient vital signs and health data to make accurate diagnosis and provide effective treatment. Obtaining insight directly from the patient provides information not easily obtained from measurement and testing alone, especially in cases of combinations or interrelated conditions. Embodiments further recognize that determining the level of engagement of a patient in responding to and communicating with healthcare providers provides an indication of the reliability and completeness of response information received from the patient. Embodiments of the present invention discussed herein are directed to a patient-provider discussion during a healthcare condition assessment of the patient to clearly and efficiently present the features of the embodiments; however, embodiments of the present invention are not limited to patient-provider assessment conversations and may be applicable to other situational conversations between individuals.

A low level of engagement of a patient, or conversely a higher level of distraction of the patient, may indicate that information provided by the patient in responses to healthcare providers is less-than accurate or incomplete. Recognition of a low level of engagement or distracted patient can be used to trigger the attending healthcare provider to make further or different inquiries or take other additional actions to fully determine the patients state of health, and not make diagnostic determinations based on incomplete or incorrect information. Understanding the level of engagement of the patient while receiving responses to the provider's questions regarding the patient's condition will avoid making a determination of the patient's condition on inaccurate or incomplete information and potentially ineffective treatment.

Embodiments of the present invention determine a probability of a level of engagement of a patient during discussion of the patient's condition with a healthcare provider. Determining a probability of engagement level to the attending healthcare provider reduces the instances of sub-optimal healthcare. Healthcare providers can optimize interactions with patients and determine the appropriate level of inquiry as to the condition and symptoms experienced by the patient to obtain a better overall view of the patient's state and diagnosis.

Embodiments generate a regression model from a plurality of historic instances of the patient's health condition or state. The respective instances of the patient's health condition include patient health information from a variety of available and consented-to sources, and responses from the patient to questions from the attending healthcare provider. Embodiments of the present invention recognize patient health information as including, but not limited to, vital signs, patient activity data, health history data, health device data (i.e., wearable devices), health application (app) data, sleep data, medication adherence data, and social media sentiment data.

The use of the phrase "level of engagement" as it refers to embodiments of the present invention in which a patient seeking healthcare assistance from a healthcare provider, refers to determining a probability that the patient communicates with the provider in an attentive manner and responds to questions directly, with clarity, thoroughness, and timeliness. A plurality of historic instances of the patient's health condition or health state refers to healthcare history of the patient in which the patient's health information was included in a record, and the attending healthcare provider made an assessment of the patient's health condition based on the health information and the patient's response to the provider's questions. The historic instances that include a record of an expert review of the patient's level of engagement during discussion with the provider serves as a ground truth health condition an establishes a ground truth of the level of patient engagement with respect to the health information and responses and observed behaviors of the patient.

In some embodiments, the dialog of historic health condition incidents between the patient and the provider, as well as the video of patient behavior and sensor data associated with the environmental conditions is obtained through a mobile smart device held by the healthcare provider. In some embodiments of the present invention, the dialog between the patient and the healthcare provider is applied to a natural language processing function and semantic analysis is performed to determine the meaning of the dialog content. In some embodiments, the analyzed dialog content may be transformed into n-grams that include subject-verb-object combinations and may include other modifiers to convey the dialog elements. In some embodiments, the dialog includes measurement indicators of time to respond and length of time of responses associated with a level of engagement as determined by an expert review during an assessment of a historic incident of the patient's health condition.

An expert review of a patient's level of engagement includes a qualified and experienced healthcare provider, such as a physician, physician assistant, nurse practitioner, and the like, conducting a health assessment of a patient, including a dialog with the patient and a recording of the level of engagement by the patient as determined by the attending provider. In some embodiments, the provider may indicate a degree of engagement by the patient, such as "fully engaged", "partially engaged", "somewhat distracted", or "very distracted", or similar degrees of engagement. In other embodiments, the provider may indicate a binary condition of engagement as "engaged" or "distracted". The expert review of a patient's level of engagement is associated with the other features included in the overall assessment of the historic health condition incident, forming a basis of a regression model that can be generated from a plurality of the patient's historic health condition incidents.

In some embodiments of the present invention, the elements of the patient health information serve as features used in generating a regression model of the level of engagement of the patient with respect to the patient health information associated with respective historic instances of the patient's health condition assessment. The assessments including ground truth expert review of the patient's level of engagement during discussion with the healthcare provider. Expert review includes information regarding the dialog between the patient and provider and observed attributes of the patient's behavior as well as the environmental conditions during the dialog, such as the number of people in the immediate area, the noise level, the activity level, the temperature in the area in which the dialog occurs.

Embodiments of the present invention include receiving a current set of patient health information and a recording or streaming of a current dialog between the patient and a healthcare provider performing the current assessment of the patient. The current set of patient health information includes a most recent collection of vital signs, wearable device data, health app data, authored social media data, as well as available health history data, all consented to by the patient. Wearable device data and health app data may include but are not limited to: data of the patient's heart rate, blood pressure, sleep activity, mobility activity, and medication adherence, and are associated with a specific instance of and assessment of the patient's health condition. The current set of patient health information also includes observed behavior of the patient and environmental conditions during the current dialog that is associated with a most recent instance of the patient's health condition in which the patient seeks service from a healthcare provider. In some embodiments, the patient behavior may include eye contact and body language positions and gestures by the patient, and environmental conditions are obtained from background video and sensors detection during the dialog.

In some embodiments of the present invention, the current set of patient health information and assessment data are applied to the generated regression model and a probability of the level of engagement of the patient for the current health assessment is determined and presented to the provider.

The provider receives the determined level of patient engagement and can determine whether the information obtained during the dialog is adequate or uncertain for accurate diagnosis and treatment, based on the engagement level indication. If the provider receives indication that the level of patient engagement is inadequate, uncertain, or the patient is otherwise distracted, then the provider may disregard some or all of the information obtained and determine alternate questions, tests or procedures to obtain more accurate information. In some embodiments, the provider may receive suggestions to pursue with the patient to improve the level of engagement.

Figure 1:
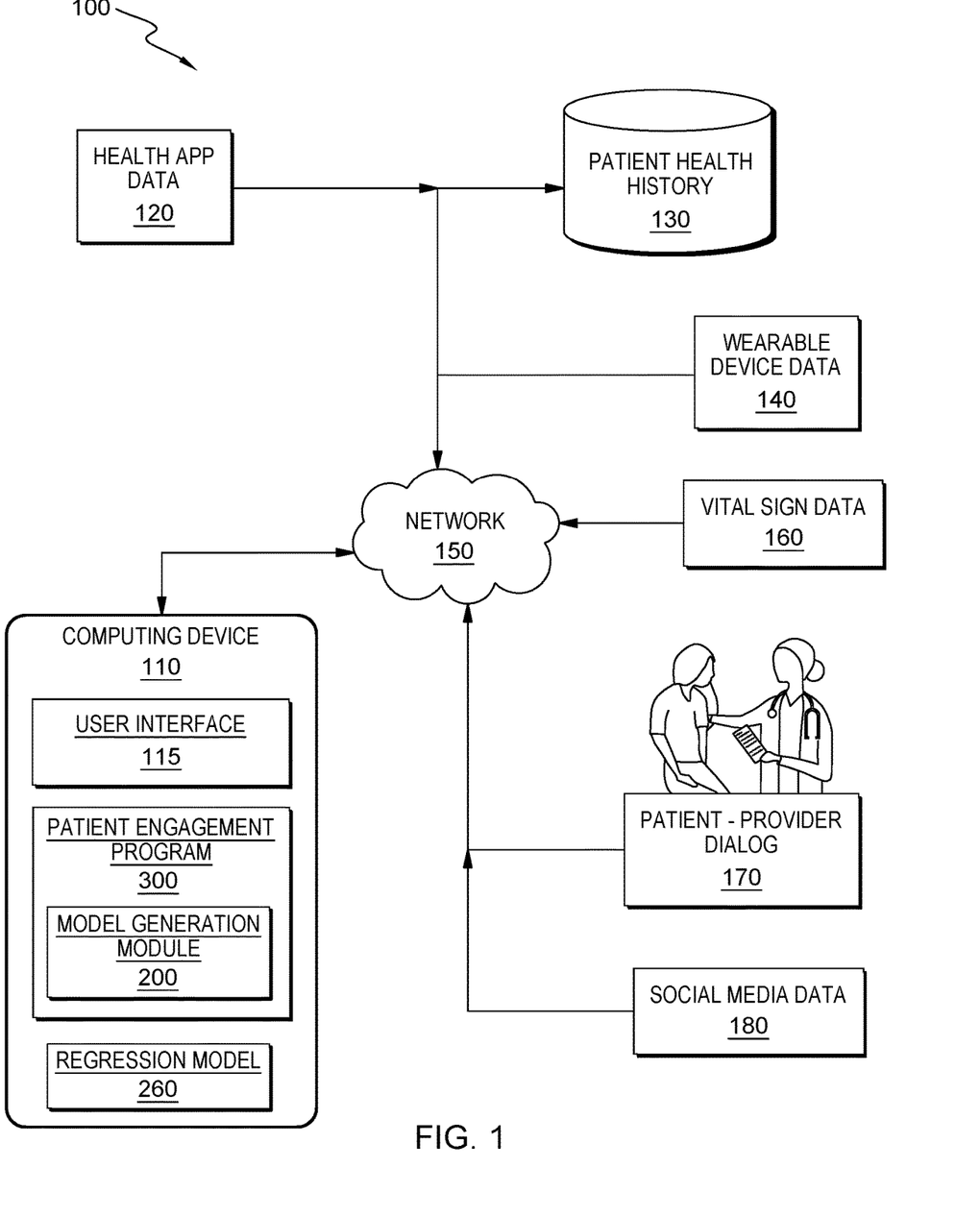
FIG. 1 is a functional block diagram illustrating a distributed data processing environment, in accordance with an embodiment of the present invention.

The present invention will now be described in detail with reference to the Figures. FIG. 1 is a functional block diagram illustrating a distributed data processing environment, generally designated 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes computing device 110, health app 120, patient health history 130, wearable device data 140, vital sign data 160 and patient-provider dialog data 170, all connected via network 150. In general, network 150 can be any combination of connections and protocols that will support communications between computing device 110, health app data 120, patient health history 130, wearable device data 140, vital sign data 160, patient-provider dialog data 170, and social media data 180, in accordance with embodiments of the present invention.

Network 150 can be, for example, a local area network (LAN), a wide area network (WAN), such as the Internet, a virtual local area network (VLAN), or any combination that can include wired, wireless, or optical connections. In general, network 150 can be any combination of connections and protocols that will support communications between computing device 110, health app data 120, patient health history 130, wearable device data 140, vital sign data 160, patient-provider dialog data 170, and social media data 180, in accordance with embodiments of the present invention.

In some embodiments of the present invention, computing device 110 is a mobile smart device and includes user interface 115, and patient engagement program 300, which further includes model generation module 200. Computing device 110 is communicatively connected to health app data 120, patient health history 130, wearable devices data 140, vital sign data 160, patient-provider dialog data 170, and social media data 180. In some embodiments, computing device 110 receives data from health app data 120, patient health history 130, wearable devices data 140, vital sign data 160, patient-provider dialog data 170, and social media data 180. The data is input to model generation module 200 of patient engagement program 300 and results in creating regression model 260 from previous (historic) patient data and previous healthcare condition assessments. By applying the most recent patient data from health app data 120, patient health history 130, wearable devices data 140, vital sign data 160, patient-provider dialog data 170, and social media data 180, to regression model 260, patient engagement program 300 determines a probability of a level of engagement of a patient in the current dialog with a healthcare provider during a current instance of a health condition assessment.

In some embodiments, computing device 110 can be a standalone mobile computing device, a smart phone, a tablet computer, a smart watch, a laptop computer, or any other electronic device or computing system capable of receiving, sending, and processing data. In other embodiments, computing device 110 can be a computing device interacting with applications and services hosted and operating in a cloud computing environment. In another embodiment, computing device 110 can be a netbook computer, a desktop computer, a personal digital assistant (PDA), or other programmable electronic device capable of communicating with health app data 120, patient health history 130, wearable devices data 140, vital sign data 160, patient-provider dialog data 170, social media data 180, and other computing devices (not shown) within distributed data processing environment 100 via network 150. In another embodiment, computing device 110 represents a computing system utilizing clustered computers and components (e.g., database server computers, application server computers, etc.) that act as a single pool of seamless resources when accessed within distributed data processing environment 100. Computing device 110 includes internal and external hardware components, depicted in FIG. 4.

User interface 115 provides an interface to access features and functions of computing device 110. In some embodiments of the present invention, user interface 115 provides access to patient engagement program 300 and model generation module 200, operating on computing device 110. User interface 115 also supports access to other applications, features, and functions of computing device 110 (not shown). User interface 115 supports access to alerts, notifications, and other forms of communications. In one embodiment, user interface 115 may be a graphical user interface (GUI) or a web user interface (WUI) and can receive user input and display text, documents, web browser windows, user options, application interfaces, and instructions for operation, and include the information (such as graphic, text, and sound) that a program presents to a user and the control sequences the user employs to control the program. In another embodiment, user interface 115 may also be mobile application software that provides an interface to features and functions of computing device 110. User interface 115 enables a user of computing device 110 to receive, view, hear, and respond to input, access applications, and perform functions available.

Health application (app) data 120 is a collection of health data from one or more applications operating on a smart device of the patient. Health app data 120 includes health data corresponding to the patient and in some embodiments of the present invention, may include a timestamp associated with the collection of the health data. In some embodiments health app data 120 is input by the patient, whereas in other embodiments health app data 120 automatically detects or receives the health data.

Figure 2:
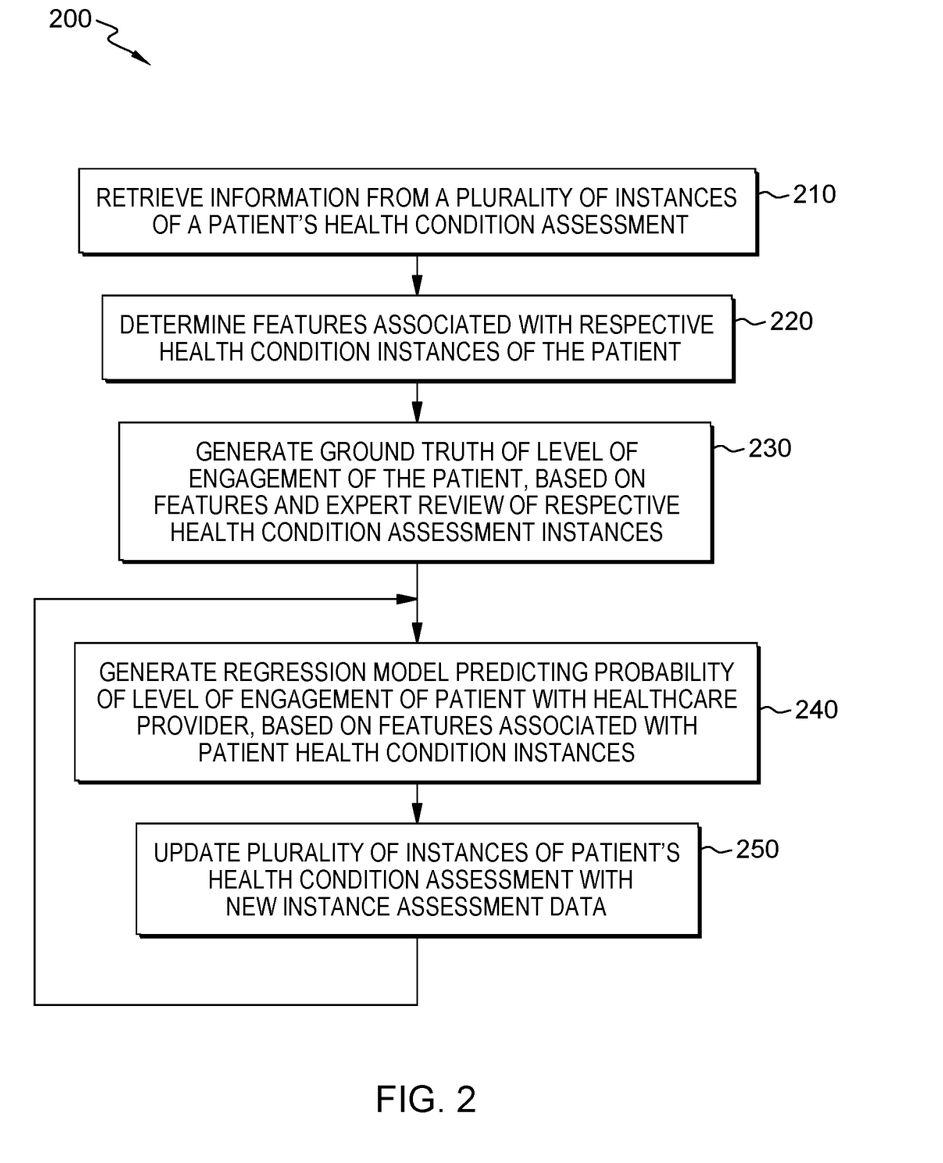
FIG. 2 illustrates steps generating a regression model as a module component of patient engagement program of FIG. 3, in accordance with embodiments of the present invention.

Model generation module 200 generates a predictive model of a patient's level of engagement in a dialog by applying an aggregate of historical patient health condition assessments that each include an engagement level determination by an expert reviewer during the assessment. The expert reviewer's determination provides a ground truth engagement level associated with the accompanying patient features included in each respective historical health condition assessment. Data elements collected from health app 120, patient health history 130, wearable device data 140, vital sign data 160, patient-provider dialog data 170, and social media data 180, individually or in combination, become features within regression model 260. Classifications are applied to features as joint classifications or multiple linear regressions. The features and classifications are applied in a linear regression format to model generation module 200 to generate regression model 260 and fit a line to the features and classifications. The fit of the regression line can be improved by applying weights to features and combining features.

Figure 3:
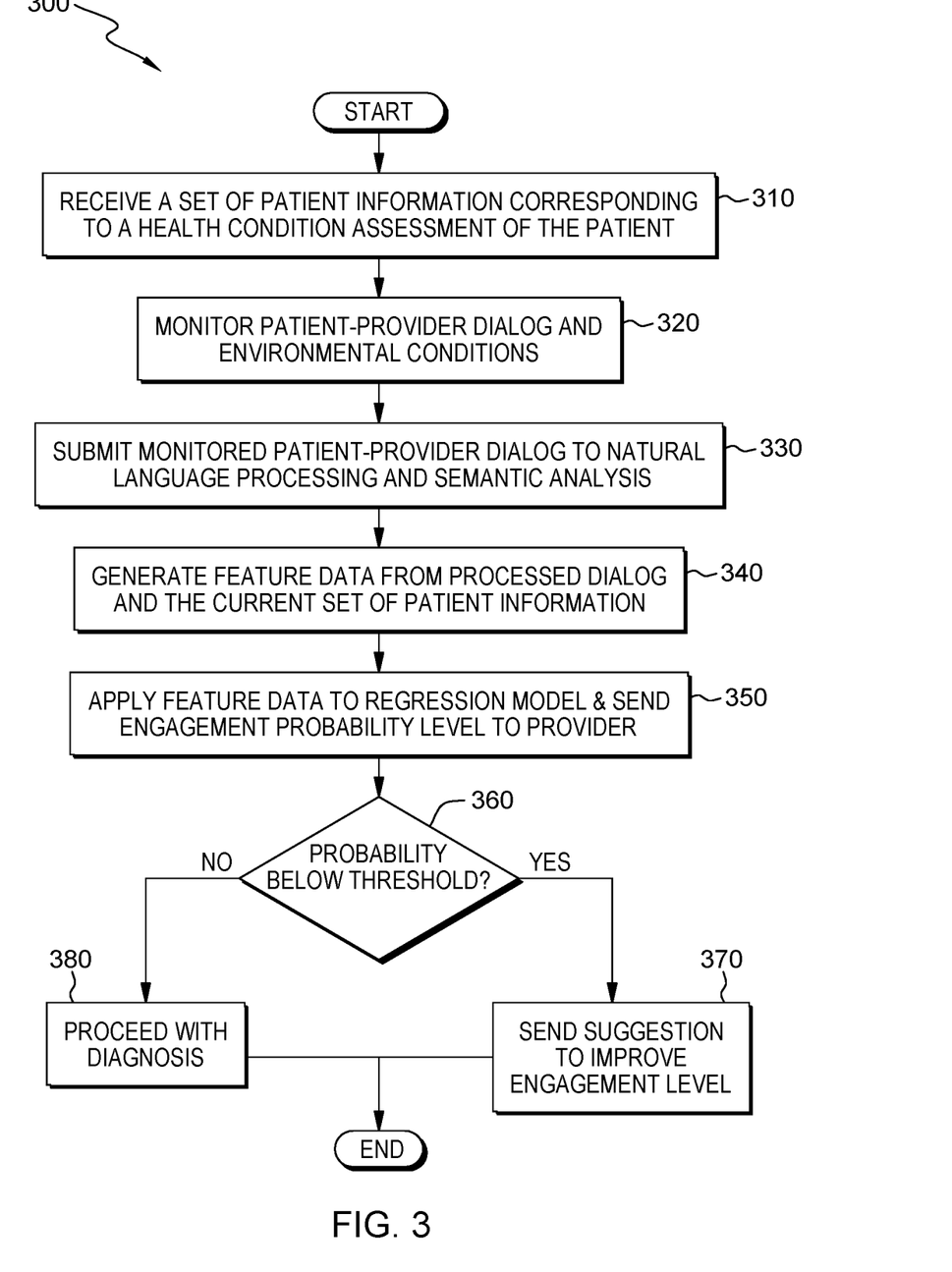
FIG. 3 is a flowchart depicting operational steps of a patient engagement program, operating in the distributed data processing environment of FIG. 1, in accordance with embodiments of the present invention.

Patient engagement program 300 operates on computing device 110 and is communicatively accessible to the healthcare provider. Patient engagement program 300 includes model generation module 200 that receives previous health information and previous health condition assessment data of the patient that include expert review of the patient's level of engagement and generates regression model 260. Patient engagement program 300 receives a current (most recent) set of patient health information and health condition assessment dialog data and applies the information and data as a collection of features to regression model 260, which results in a probability of the patient's level of engagement during the current health condition assessment of the patient by the provider.

In some embodiments of the present invention, with provided patient consent, patient engagement program 300 receives current patient health information from external sources, such as health app 120, patient health history 130, wearable device data 140, vital sign data 160, patient-provider dialog data 170 and social media data 180. Patient engagement program 300 forms feature sets from the received patient health information and applies the feature sets of the current health information to regression model 260, which results in a probability of the level of engagement of the patient during the health condition assessment.

In some embodiments, the determined probability is presented as the level of engagement. In some embodiments the engagement of the patient may be segmented into degrees of engagement, such as "very engaged", "slightly engaged", "slightly distracted", "very distracted". In other embodiments, the level of engagement may be binary in which the level of engagement exceeding a predetermined probability is determined to be "engaged", and below which the level of engagement is determined to be "distracted." Patient engagement program 300 indicates the determined level of engagement to the provider attending to the patient's current health condition assessment. In some embodiments, patient engagement program 300 provides suggested alternatives to the provider in response to determining the level of engagement of the patient to be below a predetermined threshold level (probability).

Patient health history 130 is a repository of patient health information aggregated from multiple sources. Patient health history 130 includes historic health condition assessments of the patient and the health data obtained from health app data 120, wearable device data 140, vital sign data 160 and patient-provider dialog data 170. Patient health history 130 is communicatively connected to patient engagement program 300 and model generation module 200. In some embodiments, subsequent to determining a level of engagement of a patient's current health condition assessment, the patient's health data corresponding to the assessment and the engagement level information are sent and stored in patient health history 130.

Wearable device data 140 includes health and activity related data captured from the patient's wearable device. In some embodiments of the present invention, wearable device data 140 includes some or all of the following patient data and may associate the data with a timestamp: heart rate, blood pressure, breathing rate, body temperature, walking activity, climbing activity (steps), sleep activity, calories burned, active time, and location data. In some embodiments, wearable device data 140 is communicatively connected to computing device 110 and patient engagement program 300.

Vital sign data 160 includes patient biometric measurements taken during an instance of patient health condition assessment, such as when attended to by a healthcare provider. Vital sign data 160 includes a set of vital sign data corresponding to a particular health condition assessment as a function of time, which includes historical incidents of health condition assessment, and may include a current (most recent) health condition assessment. Certain vital signs, alone or in combination, such as blood pressure, heart rate, breathing rate, and in some cases, pupil dilation, may indicate physical and emotional levels that can affect attention and focus of the patient. Vital sign data 160 may include, but is not limited to heart rate, blood pressure, body temperature, respiration rate, and pupil dilation. In some embodiments, vital sign data 160 is received by patient engagement program 300 operating on computing device 300, and receipt may be supported by automatic wireless connections with vital sign measurement devices linked to computing device 110. In other embodiments, vital sign data 160 is input to patient engagement program 300 operating on computing device 110 by a healthcare provider as the user of computing device 110.

Patient-provider dialog data 170 includes the dialog content exchange between the patient and a healthcare provider attending to the patient during an instance of health condition assessment. In some embodiments of the present invention, patient-provider dialog data 170 also includes the environmental conditions during the health condition assessment, such as noise level, people in the immediate area, activity in the immediate area, and temperature. In some embodiments, patient eye movement and body movements are monitored as additional data in determination of a level of engagement or distraction of the patient, in addition to the patient's responses to provider questions during the dialog. In an exemplary embodiment, the patient monitoring during the health condition assessment includes collection of noise data and dialog content by a microphone component of computing device 110 (not shown), the eye and body movement are captured by a camera component of computing device 110.

In some embodiments, dialog content between the patient and healthcare provider is submitted to natural language processing and semantic analysis to determine the topic and meaning associated with each exchange in the dialog. In some embodiments, the analyzed dialog content may be transformed into n-grams that include subject-verb-object combinations and may include other modifiers to convey the topic and meaning of dialog elements. In some embodiments, the dialog includes measurement indicators of time to respond and length of time of responses associated a question from the provider during an assessment. In some embodiments, the natural language processing and semantic analysis is performed by components of patient engagement program 300, whereas in other embodiments, the natural language processing and semantic analysis may be performed external to, but connectively linked to computing device 110.

Social media data 180 includes patient-consented access to social media content authored by the patient and may include content viewed and/or responded to by the patient, providing sentiment as a factor in the overall assessment of patient engagement or distraction. The data in social media data 180 is processed by sentiment and semantic analysis via patient engagement program 300 and provide topic and sentiment data for patient engagement level determination. In some embodiments of the present invention, social media sentiment provides an indicator of wellness by changing language around a topic, oscillation between negative/angry and happy emotional states, and can give trend indication. Social media data 180 provides a factor in the overall evaluation of the engagement level of the patient and may identify factors contributing to distraction.

In some embodiments of the present invention, patient information received from the various data sources is federated based on time and includes previous (historic) patient information on which regression model 260 is based, and the most recent data corresponding to a timeframe in which a current instance of condition assessment is performed by a healthcare provider. In some embodiments, current data sets of patient information showing significant deviation from "normal" baseline information are identified as features and included in patient engagement level assessment. In some embodiments, a threshold of deviation from normal baseline information may include one or more standard deviation units from a normal baseline condition. In embodiments in which the patient information lacks normal baseline condition levels, categorization of the patient may be used, and standard baseline conditions applied. For example, the patient may be categorized as 18-30 years of age, female, medium physical activity, standard weight for height, lives in Northeastern U.S. and does not travel abroad. A standard set of patient information levels for such categorization may be applied.

FIG. 2 illustrates process steps of model generation module 200 as a component of patient engagement program 300, directed to the function of generating a predictive regression model, in accordance with embodiments of the present invention. Model generation module 200 is an iterative process, continuously updating healthcare condition assessment data to improve regression model 260. Patient engagement program 300, via model generation module 200, retrieves information from a plurality of previous instances of a patient's health condition assessment history (step 210). In embodiments of the present invention, patient engagement program 300 and model generation module 200 are communicatively connected to sources of the patient's previous health condition assessments, which includes online accessible healthcare history records, wearable device data records, data recorded from the patient's health apps, vital sign data recorded during health condition assessments and information associated with patient-provider dialogs during respective previous assessments.

For example, data from patient health history 130, health app data 120, wearable device data 140, vital sign data 160, and data from patient-provider dialog data 170 is retrieved and input to model generation module 200. In some embodiments each instance of a plurality of patient health condition assessment data is associated with timestamp data to associate the aggregated data with respective instances.

Model generation module 200 determines features associated with respective health condition instances of the patient (step 220). In some embodiments, model generation module 200 determines the type of data retrieved from the plurality of health data sources of the patient and establishes types of data as features associated with respective instances of health condition assessment of the patient. In some embodiments, model generation module 200 combines types of data into a feature. In an example embodiment, model generation module 200 determines data types of blood pressure, heart rate, body temperature, activity level (steps), and sleep level baseline from wearable device data 140, medication adherence from health app 120, additional blood pressure, pulse rate and body temperature data from vital sign data 160 at the time of a health condition assessment, and dialog elements from patient-provider dialog data 170. Model generation module 200 assigns the data as features associated with the respective instances of health condition assessment of the patient and may include a baseline level of features not associated with a particular instance of health condition assessment.

Model generation module 200 generates ground truth of a level of engagement of the patient associated with respective instances of health condition assessments, based on features and expert review of respective health condition assessment instances (step 230). Model generation module 200 associates an expert review by a certified attending provider of the patient's engagement level at the time of health condition assessment for respective instances. The expert review confirms an engagement level of the patient for the respective health condition assessment and the engagement level as assessed by the provider's expert review is associated with the features determined for the respective instance. A correspondence is established with the features of each instance of patient health condition assessment and the level of engagement as determined by the expert review, forming a ground truth. Model generation module 200 generates ground truth of the patient's level of engagement for the plurality of historic instances of health condition assessment.

In some embodiments, certain better-known relationships between specific factors and engagement level, determined by univariate analysis, may provide for a simplified set of features considered for the regression model. For example, in some cases poor sleeping patterns or sleeping patterns deviating from established baseline levels for a patient correlate with lower levels of attention and engagement. Similarly, frequent loss of eye contact between the healthcare provider and the patient may also correlate with lower levels of engagement. Univariate analysis between variables specific to the level of engagement by a patient during a health condition assessment provides valuable insight in establishing weighted values and features to include in a multivariate regression model. Embodiments of the present invention recognize that a danger of overfitting a statistical model may exist in cases of models having more parameters than can be justified by the data. Embodiments of the present invention applying data determined by univariate analysis provide insight into inclusion and weighting of features of the regression model, avoiding overfitting while maintaining higher levels of predictability.

Model generation module 200 generates a regression model predicting a probability of a level of engagement of the patient with an attending healthcare provider, based on features associated with patient health condition assessment instances (step 240). Model generation module 200 applies classifications to the features, which may be individual classifications, joint classifications, or represented in multiple linear regressions. The features and classifications are applied in a linear regression format to generate a model and a line is fit to the features and classifications. The fit of the regression line can be improved by applying weights to features and by combining features. In some embodiments, the regression model fit to features and classification data provides a probability of the level of engagement of the patient during the health condition assessment, based on the patient information determined during the condition assessment. In some embodiments the determined probability is sent to the healthcare provider as an engagement level score.

For example, the features, classifications and ground truth expert review of the patient's level of engagement for respective instances of health condition assessment are processed into a linear regression format, generating a regression model that fits a line to the feature and classification data points and expert review level of engagement during previous health condition assessments. In some embodiments, multiple linear regressions are generated and are based on estimated lines for many different features. Model generation module 200 establishes and applies weighted values to features to improve subsequent classification and regression fit for engagement level prediction.

In some embodiments, the level of engagement predicted by regression model 260 is presented as a probability. In other embodiments the level of engagement of the patient may be presented as a binary condition, based on a predetermined threshold of probability. In yet other embodiments, the level of engagement may include multiple levels based a hierarchy of predetermined thresholds. For example, a level of "very engaged" may align with probabilities of greater than 70%; a level of "slightly engaged" may align with probabilities less than 70% but greater than 50%; a level of "slightly distracted" may align with probabilities of less than 50% but greater than 30%; and probabilities below 30% may be aligned with a "very distracted" level of engagement.

Model generation module 200 updates the plurality of instances of the patient's health condition assessments with a new instance of assessment data (step 250). In some embodiments of the present invention, the health condition assessment data and the probability associated with the level of engagement of the patient during the assessment is included into regression model 260 to provide continual input for model improvement. In some embodiments of the present invention, the level of engagement of the patient is predicted using patient similarity to prior engagements and predictions. The level of engagement may also be predicted prior to the first interaction using data from a survey presented to a prior healthcare provider, from a prior health condition assessment, or prior health condition survey.

FIG. 3 is a flowchart depicting operational steps of patient engagement program 300, operating in distributed data communications environment 100, in accordance with embodiments of the present invention. In embodiments of the present invention, patient engagement program 300 determines a probability of the level of engagement of a patient receiving a heath condition assessment by a healthcare provider and sends an indicator of the probability of the level of engagement of the patient to the healthcare provider. The patient information received by patient engagement program 300 are assigned as features and may be joined or combined into vectors having multiple features as distinct dimensions of the vectors, and referred to as distraction vectors, which may be categorized into primary distraction vectors, which are directly associated with biometric or controlled behavioral attributes of the patient, or secondary distraction vectors, which are features which may affect the patient but are out of the direct control or influence of the patient.

Patient engagement program 300 receives a set of patient information corresponding to a health condition assessment of the patient (step 310). In some embodiments of the present invention, patient engagement program 300 receives patient information from health apps, wearable devices, health history and social media content that include a current or recent set of data regarding the patient and associated with the patient's current health condition. Health app data may include medication adherence records, self-assessment notes by the patient, and any self-administered treatments by the patient. Wearable device data may include heart rate, blood pressure, activity level, sleep activity, and body temperature, all as a function of time, trend or a particular instance identified by date. Patient information received from a history record of the patient may include previous health conditions and treatments, vital sign data may be collected during the current health condition assessment, and social media content may be received, with patient consent, and processed to determine topic and sentiment that may relate to the patient's health condition and emotional state.

For example, patient engagement program 300 receives patient health app data 120 that includes the recent record of the patient's medication adherence, notes the patient added related to the current condition and the patient's actions addressing the condition. Patient engagement program 300 receives historic condition and treatment data from patient health history 130 and receives recent patient biometric data from wearable device data 140. Patient engagement program 300 receives current and historic vital signs measurements from vital sign data 160 and determines deviations of the current condition of the patient from normal baseline levels. Patient engagement program 300 also receives content from social media data 180 that includes content authored by the patient and topic data viewed, responded to, and commented on by the patient, with patient consent.

Patient engagement program 300 monitors patient-provider dialog and environmental conditions of the assessment (step 320). During the health condition assessment of the patient by the healthcare provider, the audible discussion is monitored by patient engagement program 300, having informed the patient of the monitoring activities and receiving patient consent. In some embodiments of the present invention, the dialog is recorded, whereas in other embodiments, the dialog between the patient and healthcare provider is live-streamed to processing functions of patient engagement program 300. In some embodiments, monitoring of the assessment dialog includes video monitoring of the patient and may include immediate environmental conditions of the assessment, such as other people present, noise level, and activity within the immediate environment. In some embodiments, the environmental temperature and other environment conditions are including in the monitored data of the assessment.

For example, patient engagement program 300 monitors the questions and responses between the healthcare provider and the patient during the health condition assessment. Patient engagement program 300 includes video monitoring of the patient, and may include patient eye-contact, body position, and body language movement during patient responses. Patient engagement program 300 determines whether other people are detected within the immediate environment of the assessment and determines whether there is high, average, or low levels of activity, noise, confusion, or other environmental conditions that may contribute to affecting attentiveness of the patient during the assessment dialog with the healthcare provider. In some embodiments, patient engagement program 300 may receive sensor-base data from computing device 110 indicating the temperature and humidity level of the environment in which the assessment takes place.

Patient engagement program 300 submits monitored patient-provider dialog to natural language processing and semantic analysis (step 330). In some embodiments of the present invention, patient engagement program 300 includes natural language processing and semantic analysis functions and submits the monitored patient-provider dialog to determine the features of the patient's responses to healthcare provider questions regarding the patient's health condition. In some embodiments, patient engagement program 300 determines the topics of the questions asked by the provider, and the meaning of respective patient's responses. In some embodiments, patient engagement program 300 also determines a response time between the delivery of the provider question and the patient's response, detecting delay, repetition, and incomplete or unrelated responses.

In other embodiments, patient engagement program 300 is communicatively connected to services providing natural language processing and semantic analysis functions (not shown) and transmits the dialog data to the connected services and receives the analysis results. In some embodiments, video data of the patient health condition assessment is analyzed for eye contact and body language data contributing to determination of the level or engagement of the patient during the health condition assessment.

For example, a healthcare provider in possession of computing device 110 on which patient engagement program 300 operates begins a dialog with a patient seeking a health condition assessment. Patient engagement program 300 records the audio and video of the assessment exchange between the patient and healthcare provider, including the questions from the healthcare provider and the responses, response time, delay, repetition, eye contact, and body language of the patient. Additionally, computing device 110 may determine the temperature and humidity of the environment in which the health condition assessment of the patient is conducted, and may provide for analysis, the background noise, activity and detection of others present in the immediate area of the assessment.

Patient engagement program 300 generates feature data from process dialog and the current set of patient information (step 340). Patient engagement program 300 receives the processed data from the dialog and environmental conditions of the health condition assessment of the patient from natural language processing and semantic analysis functions, and in some embodiments, includes eye contact and body language analysis of the patient during the assessment dialog. In some embodiments, patient engagement program 300 monitors the noise level by a microphone included in computing device 110, the temperature of the immediate environment from sensors in computing device 110, additional people present by optical recognition features associated with a camera function of computing device 110, which also determines the background movement of the environmental conditions during the health condition assessment of the patient.

The received data processed from the patient-provider dialog are included in generation of feature data associated with the health condition assessment of the patient. Also included in the generation of feature data is the patient information received from health apps, wearable devices, health history, vital sign measurements and recent social media content. The data are included as features associated with the current health condition assessment of the patient.

For example, patient engagement program 300 receives the data from processing the dialog and video data of the patient-provider assessment, as well as the environmental conditions detected during the assessment. In the example embodiment, the processed dialog data indicates a delay in the patient's response to the provider's questions, and repetition of questions resulting in a variation of responses. The example embodiment indicates the patient eye contact is poor and moving in directions away from the healthcare provider, and the environmental data indicates multiple people in the immediate area with a high level of noise and background movement, and a room temperature of 81 degrees Fahrenheit with a humidity of 79 percent. Wearable device data 140 of the example embodiment indicates a low amount of sleep by the patient, with elevated heart rate and temperature during the last 48 hours. Each element of patient information and assessment dialog are considered as features of the patient's current health condition assessment. In the example embodiment, the dialog features associated with eye contact, response rate and repetition of questions are given increased weight.

Having generated feature data, patient engagement program 300 applies the feature data to a regression model and sends engagement probability to the healthcare provider (step 350). Patient engagement program 300 applies the features generated from the health condition assessment of the patient to the regression model and determines a probability of the engagement level of the patient during the healthcare assessment, in real time, or near-real time. In some embodiments of the present invention, patient engagement program 300 sends the determined probability of the patient's level of engagement to the healthcare provider as an engagement score, via the display of computing device 110 operated by the healthcare provider.

Patient engagement program 300 determines whether the engagement level probability is below a predetermined threshold (decision step 360). Patient engagement program 300 compares the determined probability of the level of engagement of the patient for the current health condition assessment to a predetermined threshold probability to determine whether the engagement level probability falls below the threshold. For the case in which the engagement level probability exceeds the predetermined threshold (step 360, "NO" branch), patient engagement program 300 continues conducting and completing a diagnosis associated with the health condition assessment of the patient (step 380), having determined that the level of engagement of the patient was adequate to proceed.

For the case in which the engagement level probability falls below the predetermined threshold (step 360, "YES" branch), patient engagement program 300 sends a suggestion to the healthcare provider to improve the engagement level of the patient (step 370). The suggestion may include a type or line of questioning to reduce the distraction of the patient or engage them with a topic determined from the recent patient information, such as a lack of sleep, or event identified in social media content. In some embodiments of the present invention, if the engagement score is below the predetermined threshold, then patient engagement program 300 may stop the provider from completing entry of information into an electronic health record and may provide pop-up notification alerting the provider to reconfirm their assessment.

In some embodiments, patient engagement program 300 prompts the provider for common workarounds based on the data or lack of data, providing a common question suggestion related to the most pronounced feature item or lack of feature item from the health condition assessment of the patient. In response to an engagement score below the predetermined threshold probability level of engagement, patient engagement program 300 displays the engagement score and comparison to the predetermined threshold, delays entry of electronic health record data until the assessment is re-evaluated and confirmed by the provider, provides one or more suggestions of questioning to improve the engagement level of the patient or directs engagement to a different direction to improve dialog responses of the patient.

For example, the predetermined threshold probability of the patient's level of engagement is 60 percent. Applying the features determined from recent patient information and the patient's health condition assessment dialog and environmental conditions, in the example embodiment, results in a probability of 40 percent, determined by a product of features given values that may range from 1.0 to 0.01 and with some features given additional weighting. The 40 percent level of engagement of the patient falls below the predetermined threshold of 60 percent, and patient engagement program 300 sends the level of engagement probability of 40 percent (and the threshold value of 60 percent) to the healthcare provider. Patient engagement program 300 sends the determined 40 percent engagement level probability to the healthcare provider along with the comparable threshold level of 60 percent. Patient engagement program 300 also sends a suggestion prompt to the healthcare provider to inquire about the patient's ability to get adequate sleep and whether the patient would prefer to discuss their condition in another room.

Figure 4:
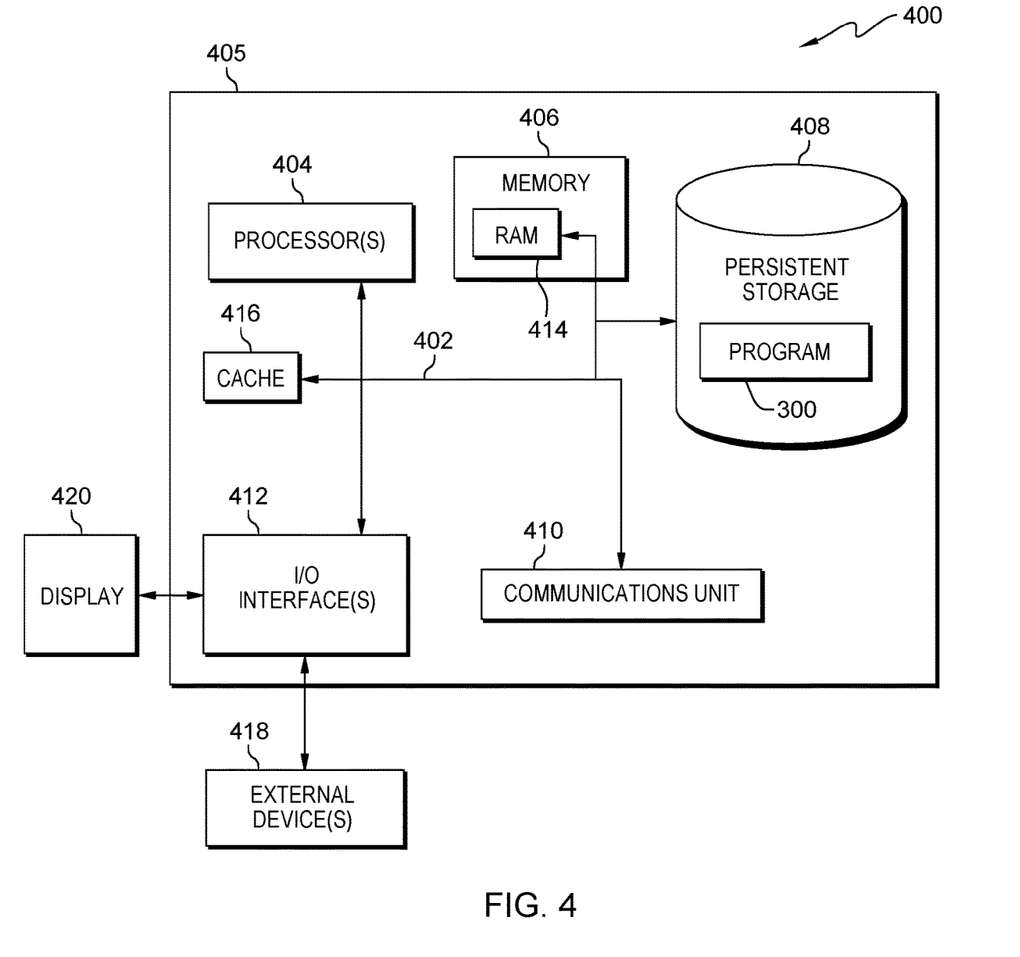
FIG. 4 depicts a block diagram of components of a computing system, including a computing device configured with capability to operationally perform the patient engagement program of FIG. 3, in accordance with an embodiment of the present invention.

FIG. 4 depicts a block diagram of components of computing system 400, including computing device 405, configured to include or operationally connect to components depicted in FIG. 1, and capable of performing operational steps of model generation module 200 and patient engagement program 300 of FIG. 3, in accordance with an embodiment of the present invention, in accordance with an embodiment of the present invention.

Computing device 405 includes components and functional capability similar to components of calling device 110 (FIG. 1), in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Computing device 405 includes communications fabric 402, which provides communications between computer processor(s) 404, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406, cache memory 416, and persistent storage 408 are computer readable storage media. In this embodiment, memory 406 includes random access memory (RAM) 414. In general, memory 406 can include any suitable volatile or non-volatile computer readable storage media.

In one embodiment, regression model 260 and patient engagement program 300 are stored in persistent storage 408 for execution by one or more of the respective computer processors 404 via one or more memories of memory 406. In this embodiment, persistent storage 408 includes a magnetic hard disk drive. Alternatively, or in addition to a magnetic hard disk drive, persistent storage 408 can include a solid-state hard drive, a semiconductor storage device, read-only memory (ROM), erasable programmable read-only memory (EPROM), flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices, including resources of distributed data processing environment 100. In these examples, communications unit 410 includes one or more network interface cards. Communications unit 410 may provide communications through the use of either or both physical and wireless communications links. Model generation module 200 and patient engagement program 300 may be downloaded to persistent storage 408 through communications unit 410.

I/O interface(s) 412 allows for input and output of data with other devices that may be connected to computing system 400. For example, I/O interface 412 may provide a connection to external devices 418 such as a keyboard, keypad, a touch screen, and/or some other suitable input device. External devices 418 can also include portable computer readable storage media such as, for example, thumb drives, portable optical or magnetic disks, and memory cards. Software and data used to practice embodiments of the present invention, e.g., model generation module 200 and patient engagement program 300 can be stored on such portable computer readable storage media and can be loaded onto persistent storage 408 via I/O interface(s) 412. I/O interface(s) 412 also connect to a display 420.

Display 420 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for determining a level of engagement of a patient with a provider, the method comprising:
   one or more processors retrieving previous health information of a patient and including a plurality of previous instances of health condition assessments of a patient;
   the one or more processors generating ground-truth health conditions of the patient, based on an assessment performed on the plurality of previous instances of the health condition of the patient, respectively, in which the assessment includes the health information of the patient, an expert review of a level of engagement of the patient, observations of the patient including eye contact, body language, response time to provider's questions, response repetition, and monitoring of environmental conditions that include background noise, activity, and detection of others present at the time of the assessment;
   the one or more processors generating a regression model predicting a probability of the level of engagement of the patient based on the respective assessments performed on the plurality of previous instances of the health condition assessments of the patient;
   the one or more processors receiving a current set of patient health information, results of natural language processing of a dialog between the patient and a current provider performing a current assessment of the health condition of the patient, as well as observations of the patient, and monitoring of environmental conditions in which the current assessment is conducted;
   the one or more processors applying the current set of patient information, the results of the natural language processing of the dialog, observations of the patient, and the environmental conditions monitored during the current assessment, to the regression model; and
   in response to determining the probability of the level of engagement of the patient to the current provider, the one or more processors sending the probability of the level of engagement of the patient predicted by the regression model, to the current provider.

2. The method of claim 1, wherein the current set of patient health information includes vital signs, health information from wearable devices and health applications of the patient, health history from accessible electronic records of the patient, and sentiment of the patient from social media content of the patient.

3. The method of claim 1, further comprising:
   the one or more processors determining a topic and correspondence of questions by the current provider and responses by the patient by applying natural language processing and semantic analysis to the dialog between the patient and the current provider performing the current assessment of the health condition of the patient; and
   the one or more processors determining whether the responses by the patient indicate positive features of engagement of the patient to the current provider.

4. The method of claim 1, wherein the probability of the level of engagement of the patient with the current provider is based on one or a combination selected from a group consisting of: the current set of patient information including sleep patterns, the environmental conditions monitored during the current assessment of the health condition of the patient, and the dialog between the patient and the current provider.

5. The method of claim 1, further comprising:
the one or more processors monitoring the dialog between the patient and the current provider by streaming audible content of the dialog between the patient and the current provider to the natural language processing and a semantic analysis; and
the one or more processors monitoring a noise level, temperature, additional people present, and background movement of the environmental conditions during the current health condition assessment of the patient.

6. The method of claim 1, further comprising:
the one or more processors providing a suggestion of questioning to the current provider to improve the level of engagement of the patient; and
the one or more processors delaying an entry of the current assessment of the health condition of the patient into electronic health records until the current provider reconfirms a diagnosis associated with the current assessment of the health condition of the patient.

7. The method of claim 1, wherein the health information of the patient from the plurality of sources is retrieved from a combination of sources selected from a group consisting of: the patient's wearable devices, health applications, electronic health history of the patient, data from previous patient-provider dialogs, and social media data.

8. The method of claim 1, wherein the results of natural language processing of a dialog between the patient and the current provider performing the current assessment of the health condition of the patient include data determining a topic of respective questions asked by the current provider and topic, sentiment, and alignment of responses by the patient to the respective questions asked by the current provider.

9. A computer program product for determining a level of engagement of a patient with a provider, the computer program product comprising:
one or more computer readable storage media and program instructions stored on the one or more computer readable storage media, the program instructions comprising:
program instructions to retrieve previous health information of a patient and including a plurality of previous instances of health condition assessments of a patient;
program instructions to generate ground-truth health conditions of the patient based on an assessment performed on the plurality of the previous instances of the health condition of the patient, respectively, in which the assessment includes the health information of the patient, an expert review of a level of engagement of the patient, observations of the patient including eye contact, body language, response time to provider's questions, response repetition, and monitoring of environmental conditions that include background noise, activity, and detection of others present at the time of the assessment;
program instructions to generate a regression model predicting a probability of a level of engagement of the patient, based on the respective assessments performed on the plurality of previous instances of the health condition assessments of the patient;
program instructions to receive a current set of patient health information, results of natural language processing of a dialog between the patient and a current provider performing a current assessment of the health condition of the patient, as well as observations of the patient, and monitoring of environmental conditions in which the current assessment is conducted;
program instructions to apply the current set of patient health information and the dialog, observations of the patient, and environmental conditions monitored during the current assessment, to the regression model; and
in response to determining the probability of the level of engagement of the patient to the current provider, program instructions to send the probability of the level of engagement of the patient predicted by the regression model to the current provider.

10. The computer program product of claim 9, wherein the current set of patient health information includes vital signs, health information from wearable devices and health applications of the patient, health history from accessible electronic records of the patient, and sentiment of the patient from social media content of the patient.

11. The computer program product of claim 9, further comprising:
program instructions to determine a topic and correspondence of questions by the current provider and responses by the patient by applying natural language processing and semantic analysis to the dialog between the patient and the current provider performing the current assessment of the health condition of the patient; and
program instructions to determine whether the responses by the patient indicate positive features of engagement of the patient to the current provider.

12. The computer program product of claim 9, wherein the probability of the level of engagement of the patient with the current provider is based on the current set of patient information including sleep patterns, the environmental conditions monitored during the current assessment of the health condition of the patient, and the dialog between the patient and the current provider.

13. The computer program product of claim 9, further comprising:
program instructions to stream audible content of the dialog between the patient and the current provider to the natural language processing and a semantic analysis; and
program instructions to monitor noise level, temperature, additional people present, and background movement of the environmental conditions of the current assessment.

14. The computer program product of claim 9, further comprising:
program instructions to provide a suggestion of questioning to the current provider to improve the level of engagement of the patient; and
program instructions to delay an entry of the current assessment of the health condition of the patient into electronic health records subsequent to the current provider reconfirming a diagnosis associated with the current assessment of the patient.

15. A computer system for determining a level of engagement of a patient with a provider, the computer system comprising:
one or more computer processors;
one or more computer readable storage media; and
program instructions stored on the one or more computer readable storage media, the program instructions comprising:
program instructions to retrieve previous health information of a patient and including a plurality of previous instances of health condition assessments of a patient;
program instructions to generate ground-truth health conditions of the patient based on an assessment performed on the plurality of the previous instances of the health condition of the patient, respectively, in which the assessment includes the health information of the patient, an expert review of a level of engagement of the patient, observations of the patient including eye contact, body language, response time to provider's questions, response repetition, and monitoring of environmental conditions that include background noise, activity, and detection of others present at the time of the assessment;
program instructions to generate a regression model predicting a probability of a level of engagement of the patient, based on the respective assessments performed on the plurality of previous instances of the health condition assessments of the patient;
program instructions to receive a current set of patient health information, results of natural language processing of a dialog between the patient and a current provider performing a current assessment of the health condition of the patient, as well as observations of the patient, and monitoring of environmental conditions in which the current assessment is conducted;
program instructions to apply the current set of patient health information and the dialog, observations of the patient, and environmental conditions monitored during the current assessment, to the regression model; and
in response to determining the probability of the level of engagement of the patient to the current provider, program instructions to send the probability of the level of engagement of the patient predicted by the regression model to the current provider.

16. The computer system of claim 15, further comprising:
program instructions to determine a topic and correspondence of questions by the current provider and responses by the patient by applying natural language processing and semantic analysis to the dialog between the patient and the current provider performing the current assessment of the health condition of the patient; and
program instructions to determine whether the responses by the patient indicate positive features of engagement of the patient to the current provider.

17. The computer system of claim 15, wherein the probability of the level of engagement of the patient with the current provider is based on the current set of patient information including sleep patterns, the environmental conditions monitored during the current assessment of the health condition of the patient, and the dialog between the patient and the current provider.

18. The computer system of claim 15, further comprising:
providing a suggestion of questioning to the current provider to improve the engagement level of the patient; and
delaying an entry of the current assessment of the health condition of the patient into electronic health records until the current provider reconfirms a diagnosis associated with the assessment of the patient.

19. The computer system of claim 15, wherein the health information of the patient from a plurality of source is retrieved from the patient's wearable devices, health applications, electronic health history of the patient, data from previous patient-provider dialogs, and social media data.

20. The computer system of claim 15, wherein the results of natural language processing of a dialog between the patient and the current provider performing the assessment of the condition of the patient include data determining a topic of respective questions asked by the current provider and topic, sentiment, and alignment of responses by the patient to the respective questions asked by the current provider.

* * * * *